(12) United States Patent
Hollister et al.

(10) Patent No.: US 6,551,287 B2
(45) Date of Patent: Apr. 22, 2003

(54) NEEDLE PROTECTION APPARATUS USED WITH A VIAL

(75) Inventors: William H. Hollister, Nelson, NH (US); Roddi J. Simpson, Antrim, NH (US)

(73) Assignee: Portex, Inc., Keene, NH (US)

( * ) Notice: Subject to any disclaimer, the term of this patent is extended or adjusted under 35 U.S.C. 154(b) by 35 days.

(21) Appl. No.: 09/777,672

(22) Filed: Feb. 7, 2001

(65) Prior Publication Data

US 2001/0004970 A1 Jun. 28, 2001

Related U.S. Application Data

(62) Division of application No. 09/227,819, filed on Jan. 11, 1999.

(51) Int. Cl.[7] .................................................. A61M 5/00
(52) U.S. Cl. ...................................... 604/263; 604/192
(58) Field of Search ............................ 604/110, 164.08, 604/192, 263, 187, 197

(56) References Cited

U.S. PATENT DOCUMENTS

| | | | |
|---|---|---|---|
| 5,312,369 A | * | 5/1994 | Arcusin et al. ............. 604/192 |
| 5,490,841 A | | 2/1996 | Landis et al. |
| 5,843,047 A | | 12/1998 | Pyrozyk et al. |
| 5,925,032 A | * | 7/1999 | Clements ................... 604/192 |
| 6,334,857 B1 | * | 1/2002 | Hollister et al. ............ 604/192 |

* cited by examiner

Primary Examiner—Michael J. Hayes
Assistant Examiner—Catherine Serke
(74) Attorney, Agent, or Firm—Louis Woo

(57) ABSTRACT

A needle protection device for a vial has a collar at the base of which a number of finger grippers extend. The collar is placed about the hub of a vial and pushed therealong until the gripper fingers snap over the bottom surface of the needle hub so as to fixedly couple the collar to the needle hub of the vial. Flexibly extending from the collar is a housing that is pivotable to a position in alignment along the longitudinal axis of the vial for enveloping the needle, to thereby prevent the needle from being exposed to the environment. A hook integrated to the inside of the housing ensures that the needle and the housing could no longer move relative to each other once the hook snaps over and traps the needle, as the housing is pivoted to its alignment position. For those vials that have a needle hub that extends smoothly from the vial, a second embodiment of the instant invention has, in place of the collar, a base that has two extending arms with coacting ends. Once the base is slipped over the vial and positioned appropriately therealong, the arms are pressed towards each other until the two coacting ends lock into place to thereby fixedly couple the base to the vial. A housing flexibly extending from the base is pivoted to a position in alignment with the longitudinal axis of the vial for enveloping a needle that extends from the hub of the vial.

10 Claims, 4 Drawing Sheets

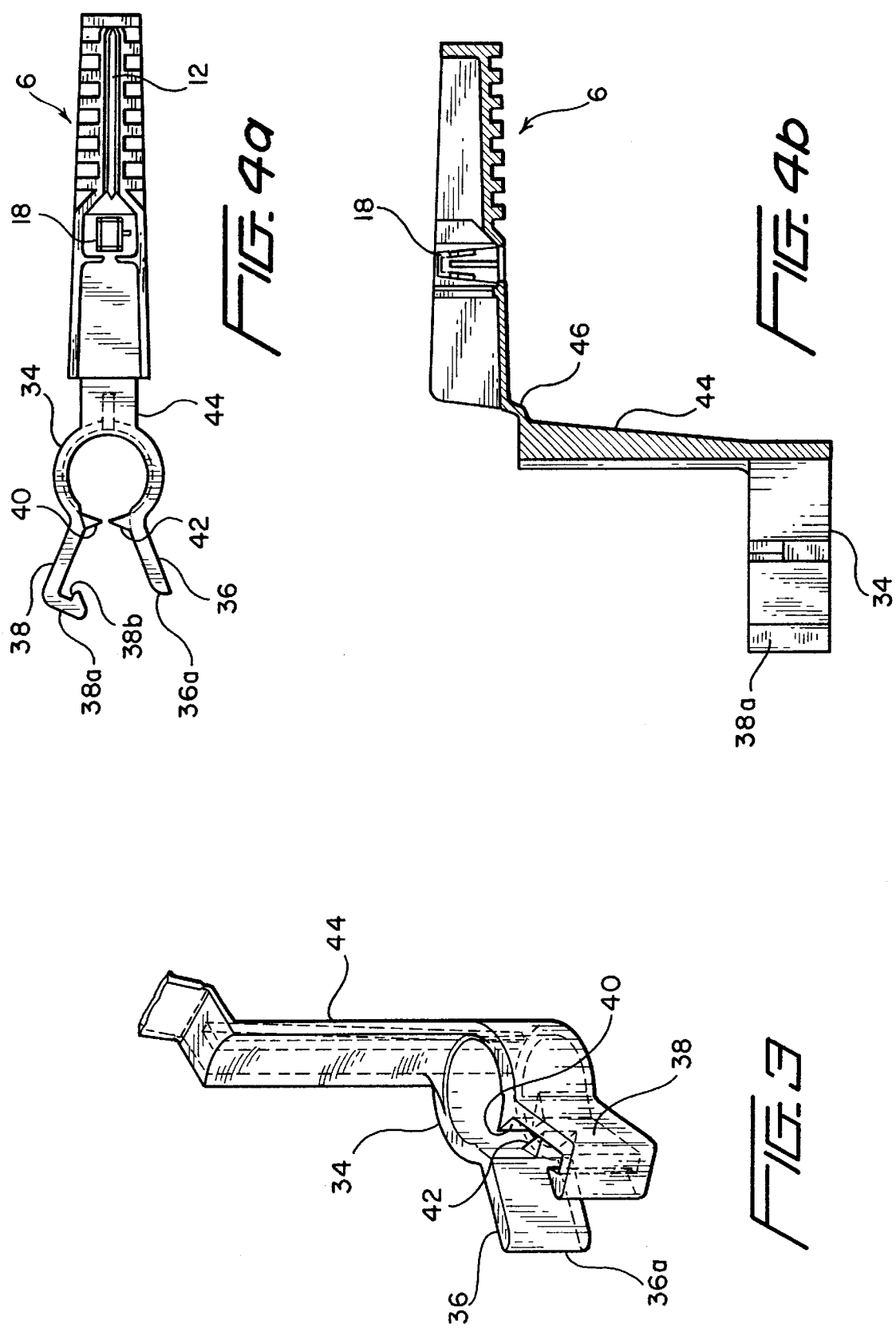

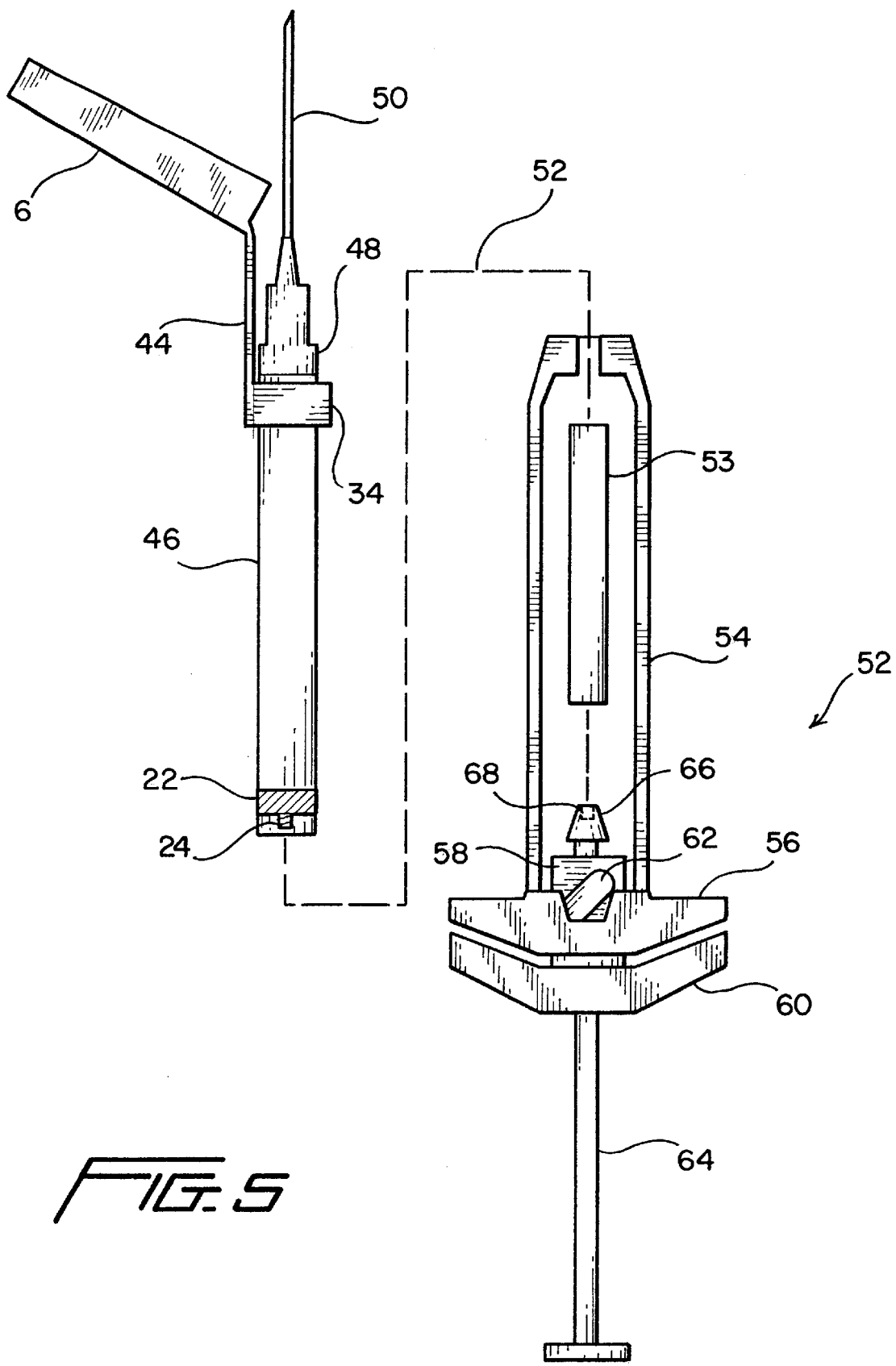

US 6,551,287 B2

NEEDLE PROTECTION APPARATUS USED WITH A VIAL

This is a division of application Ser. No. 09/227,819, filed Jan. 11, 1999.

FIELD OF THE INVENTION

The present invention relates to a needle protection device used with a vial that contains medicament to be injected to a patient, and more particularly for preventing further exposure of the contaminated needle once the medicament in the vial has been injected to the patient and the needle has been withdrawn from the patient.

BACKGROUND OF THE INVENTION

In the medical field, needle protection devices are well known. A number of such devices, assigned to the assignee of the instant invention by inventor Hollister, reference the use of a needle protection device to cover a contaminated needle. These include U.S. Pat. No. 4,982,842 that discloses a universal safety adapter for use with a syringe and a needle assembly, and U.S. Pat. Nos. 5,139,489, 5,154,285 and 5,277,311, all of which disclose, among other things, the use of a needle protection device with a VACUTAINER double ended needle. Other Hollister patents that describe needle protection devices include U.S. Pat. Nos. 5,232,454, 5,232,455, 5,423,765, 5,615,771 and 5,649,622.

There is currently in the market a number of vials, presealed with medicament such as for example heparin, that are to be injected to a patient. The use of vials that contain medicament is more efficient in some ways than the use of a syringe insofar as the amount of medicament stored in a vial has been premeasured and, since the vial is sealed, the problem of contamination substantially eliminated. Yet the fact remains that in order to inject a patient with the medicament of a vial, a needle has to be used. Oftentimes such needle is mounted to the vial during manufacturing of the vial. Examples of such needle mounted vials include those used with the Tubex and Carpuject applicators. Yet none of these vials configured with a needle has any prophylactic device that will prevent the exposure of the contaminated needle from the environment once the medicament in the vial has been injected to the patient and the needle withdrawn from the patient.

SUMMARY OF THE PRESENT INVENTION

To provide protection against accidental pricking by a contaminated needle attached to a vial, a collar that is configured to slidably fit to the needle hub of the vial is inserted over the needle hub before the needle cover is removed from the needle. The collar has extending to its lower side a number of finger extensions each of which has a hook-like gripper for mating with the bottom portion of the needle hub of the vial. Thus, when the collar is moved to the appropriate distance along the needle hub, the finger extensions would snap over the edge of the bottom portion of the needle hub so that the hooks at the end of the finger extensions will grasp onto the bottom surface of the hub. The collar, once thus secured, nonetheless is rotatable about the hub of the vial.

A housing flexibly extending from the top of the collar provides the enclosure for covering the needle extending from the vial, once the contaminated needle is withdrawn from the patient and the housing is pivoted into alignment along the longitudinal axis of the vial. A hook mechanism inside the housing locks onto the needle once the housing is pivoted into alignment with the vial and the hook mechanism comes into contact with the needle and snaps thereover.

Instead of a collar, a second embodiment of the instant invention has a non-closed substantially circular base that has two arms or ears extending away from the base. These two arms coact with each other when they are pressed towards each other. One of the arms has a hooked extension that interacts with the blunt extension of the other arm so that when the two arms are pressed together, the hooked extension will snap over the blunt extension and the two arms are interlocked. This embodiment of the instant invention is used for those vials which needle hub substantially smoothly extends from the medicament containing body. The base of the second embodiment device is therefore configured to fit over the body of the vial so that, once positioned appropriately onto the body, the arms of the base are squeezed to lock the base into position around the vial.

A housing that is similar to that used in the first embodiment is flexibly connected to a neck extending from the base. As before, to cover a contaminated needle, the housing is pivoted into alignment along the longitudinal axis of the vial to which the base is mounted about, so that the needle is covered by the housing. An integral hook in the housing grasps onto the needle and prevents any relative movement between the needle and the housing once the housing has been pivoted sufficiently to allow the hook to snap over the needle.

It is therefore an objective of the present invention to provide an add-on device that prevents a contaminated needle extending from a vial from being exposed to the environment.

It is another objective of the present invention to provide a protective device that is fixedly attached to a vial once it is fitted to the vial.

It is moreover an objective of the present invention to provide an inexpensive way of retrofitting a conventional vial such that protection is provided therefor to prevent accidental needle pricks from a needle attached thereto.

BRIEF DESCRIPTION OF THE FIGURES

The above-mentioned objectives and advantages of the present invention will become apparent and the invention itself will be best understood with reference to the following description of embodiments of the present invention taken in conjunction with the accompanying drawings, wherein:

FIG. 3 is a perspective illustration of a second embodiment of the device of the instant invention sans the housing;

FIG. 4a is a top view of the second embodiment device;

FIG. 4b is a cross-sectional side view of the second embodiment device of the instant invention; and FIG. 5 shows the vial and the injection applicator used with the second embodiment of the instant invention as illustrated in FIGS. 3 and 4.

DETAILED DESCRIPTION OF THE EMBODIMENTS OF THE INVENTION

Figure 1C:
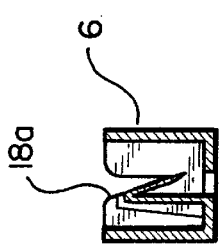
FIG. 1c is a cross-sectional side view of the housing of the FIG. 1a device.
Figure 1F:
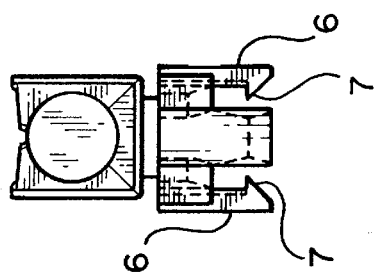
FIG. 1f is an end view of the FIG. 1d device.
Figure 1A:
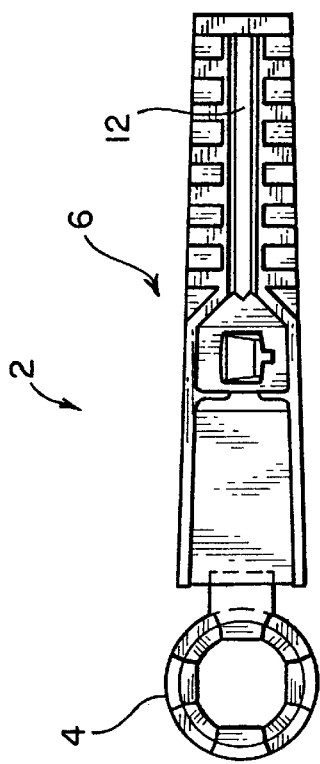
FIG. 1a is a top view of the first embodiment of the present invention with the housing pivoted at right angle to the collar of the device.
Figure 1D:
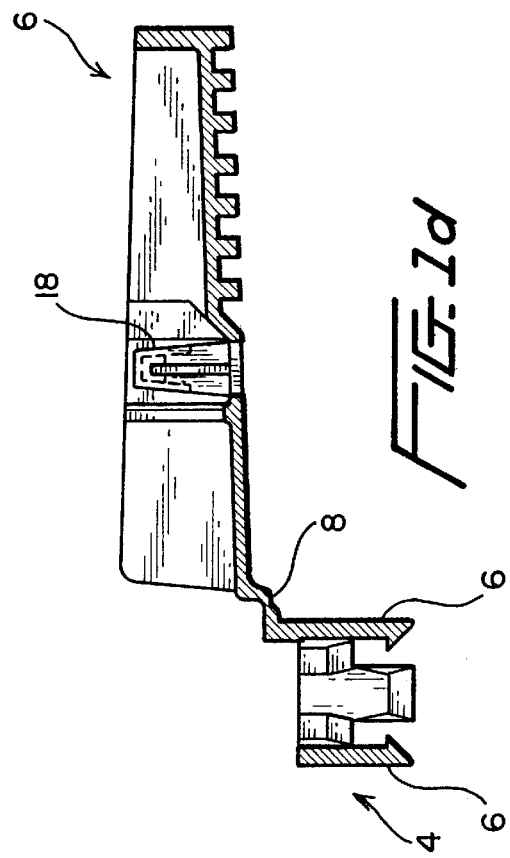
FIG. 1d is a sectional side view of the first embodiment device of the instant invention.
Figure 1B:
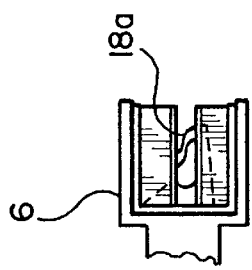
FIG. 1b is a cross-sectional view of the housing of FIG. 1a illustrating the hook therein.
Figure 1E:
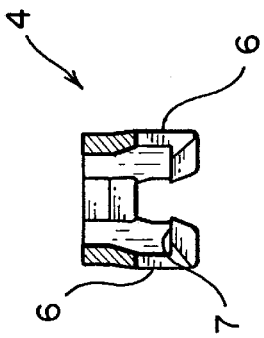
FIG. 1e is a cross-sectional view of the collar of the FIG. 1d illustration.

With reference to FIGS. 1a–1d, the needle protection device 2 of the instant invention is shown to include a collar 4 and a housing 6 flexibly attached thereto by means of a living hinge 8. As best shown in FIGS. 1d, 1e and 1f, collar 4 has a main section wherefrom a number of fingers 6 extend. At the tip of each of fingers 6 there is a hook tip 7. The size of collar 6 is configured to fit over a needle hub such as for example hub 10 shown in FIG. 2.

A second element of the needle protection device of the instant invention is housing 6 that is flexibly connected to collar 4 by means of living hinge 8. As shown, housing 6 has a longitudinal slot 12 through which a needle such as for example 12 shown in FIG. 2 can pass through when housing 6 is pivoted along the direction indicated by directional arrow 14 to a position in alignment with the longitudinal axis of a vial 16, so as to cover needle 12. Housing 6 is further shown to have a hook 18 integrated to the inside thereof so that, once housing 6 is pivoted into longitudinal alignment with vial 16, the bent portion 18a (FIG. 1b) of hook 18 will snap over needle 12 to therefore prevent any further relative movement between needle 12 and housing 6. Once needle 12 is secured by hook 18, needle 12 is prevented from being exposed to the environment, as it remains enveloped by housing 6.

Figure 2:
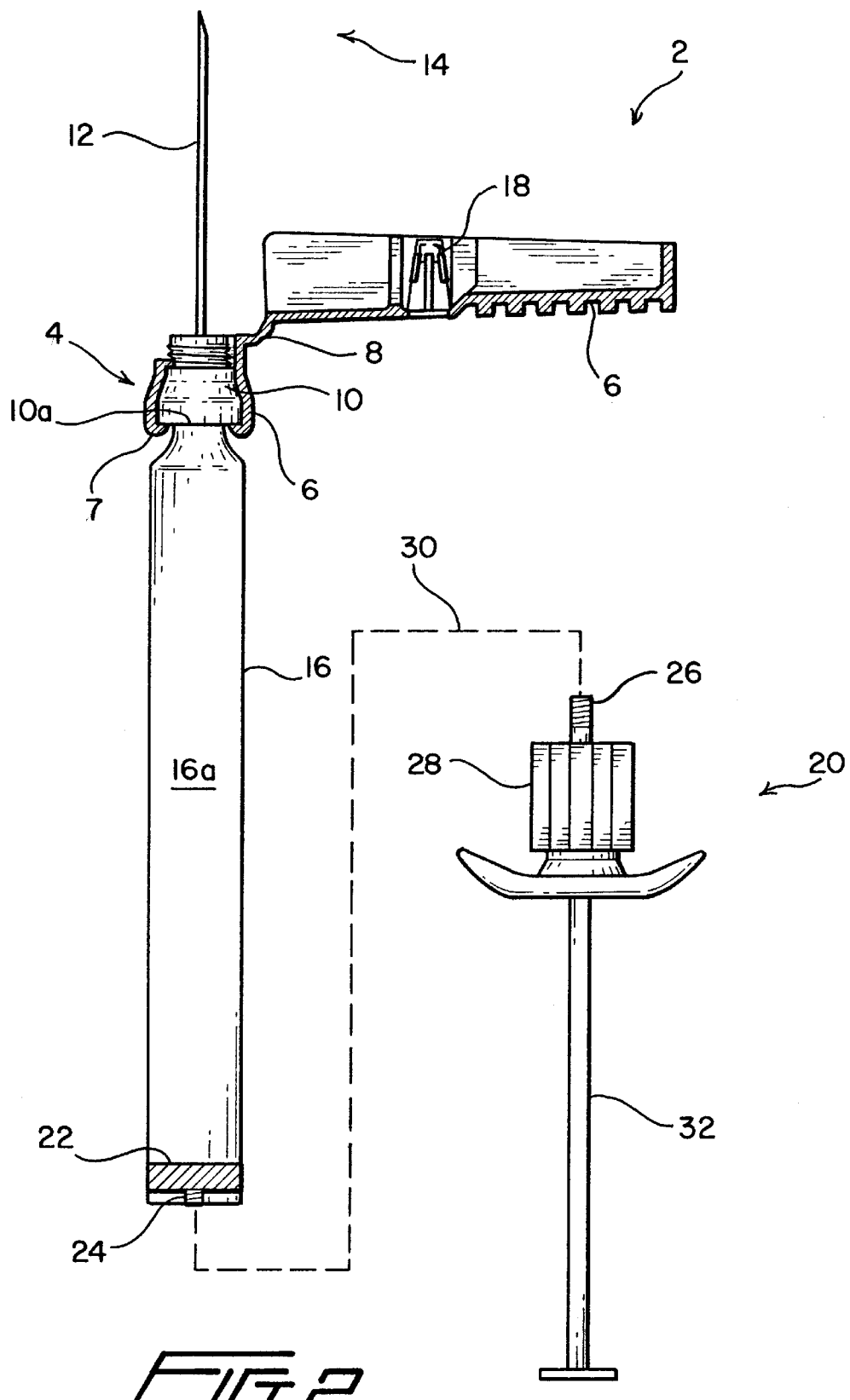
FIG. 2 is an illustration of the instant invention device having been matingly coupled to a vial, and the injection applicator that is used with the vial to enable a user to eject the medicament stored in the vial.

With specific reference to FIG. 2, note that to secure device 2 to vial 16, collar 4 is inserted about hub 10 of the needle assembly of vial 16 and pushed downward until hook tips 7 of collar 4 snap over the bottom surface 10a of hub 10. Since device 2 is made of a plastic material that has a given amount of flexibility and collar 4 is configured to fit closely to hub 10, when collar 4 is inserted about hub 10, its elasticity allows fingers 6 to expand until their respective hook tips snap over bottom surface 10a of hub 10. At which time fingers 6 will return to their natural configured state so that hook tips 7 are maintained behind bottom surface 10a to thereby fixedly coupled collar 4 to hub 10 of vial 16. Since collar 4 is coupled to hub 10 only due to the contact between hook tips 7 and the bottom surface 10a of hub 10, device 2 is rotatable about hub 10.

Vial 16 shown in FIG. 2 is a conventional type of vial that is adaptable to be mated to a Tubex type injection applicator, such as for example that designated by 20. As shown, vial 16 has a main body 16a inside of which a medicament such as for example heparin may be stored. Vial 16 is closed at its one end by hub 10 and needle 12 extending therefrom. Vial 16 is sealed at its other end by a rubber gasket 22 movable along the length of vial 16 that has molded thereto a screw 24. Screw 24 is threadedly mated to a threaded end 26 of injection applicator 20, which also has a turnable coupler that can be fitted to the end of vial 16 as shown by the dotted line 30. Once coupled to vial 16, coupler 28 is turned so as to squeezingly secure injector 20 to vial 16. Once injector 20 is securely fixed to vial 16, the combination of vial/injection applicator functions the same way as a conventional syringe. This is due to the fact that injection applicator 20 further has a plunger 32 that, by means of threaded portion 26, is threadedly coupled to rubber gasket 22, so that by pushing plunger 32 towards hub 10 along the longitudinal axis of vial 16, the medicament stored in main body 16a could be injected to a patient to which needle 12 is inserted.

As noted above, once needle 12 is withdrawn from the patient after the medicament in vial 16 has been injected to the patient, to prevent the contaminated needle 12 from being further exposed to the environment, housing 6 is pivoted in the direction as indicated by arrow 14 to envelope needle 12. Needle 12 is secured within housing 6 by means of the interaction between hook 18 and needle 12, when hook 18 snaps over and retains needle 12 within housing 6.

A second embodiment of the instant invention is illustrated in FIGS. 3, 4a and 4b. As shown in the perspective view of FIG. 3, the needle protection device has a non-close base 34 that has two arms or ears 36 and 38 extending therefrom. As shown, arm 36 has a blunt tip 36a whereas arm 38 has a hooked tip 38a. By pressing arms 36 and 38 towards each other, so that hook tip 38a snaps over blunt tip 36a, arms 38 and 36 are locked into place with respect to each other. By means of shoulders 40 and 42, arms 38 and 36 are ensured not to be forced sufficiently close towards each other so as to substantially deform the configuration of the inside circumference of base 34. Further, shoulders 40 and 42 prevent arms 38 and 36 from being inadvertently freed from each other by the further compressing of those arms towards each other.

As best shown in FIGS. 3 and 4b, extending from base 34 is a neck 44 at the end of which, by means of a living hinge 46, a housing 6 is attached. Insofar as housing 6 shown in FIGS. 3 and 4 is the same as that shown in FIGS. 1 and 2, the same elements as discussed earlier are likewise present in the housing 6 for the embodiment of the instant invention as illustrated in FIGS. 3 and 4. Accordingly, the same designations are used.

FIG. 5 illustrates the type of vial to which the needle protection device of the FIG. 3 embodiment may be used. As shown, vial 46 has a main body and a hub 48 extending substantially smoothly therefrom. Since hub 48 and vial 46 essentially forms a single body due to the smooth integration of hub 48 to vial 46, the collar of the first embodiment could not be used herein. Like vial 16, vial 46 also has a movable rubber gasket 22 at its open end that acts to seal the medicament content of vial 46 from the environment. A needle 50 extends from the end of hub 48.

A Carpuject type injection applicator 52 is further illustrated in FIG. 5. As shown, applicator 52 has a body 54 with one side thereof opened to the environment. An aperture 53 is formed at the opposed side of body 54. Housing 54 has a finger grip base 56. Inserted through base 56 is a cylinder 58 that extends from a base 60 that has a shape substantially mirrors that of base 56. Cylinder 58 has a groove 62 that mates with a bump protrusion (not shown) formed at the back side of base 56. Thus, a clinician can raise or lower cylinder 58 relative to base 56 by turning base 60 clockwise or counterclockwise, respectively. A plunger rod 64 is movably fitted to base 16 and cylinder 58. Rod 64 has an integral head 66 having therewithin a threaded portion 68 that mates with screw 24 of vial 46. Head 66 of the push rod is movable longitudinally within body 54, in response to the movement of rod 64.

As shown in FIG. 5, vial 46 is fitted with the needle protection device of FIG. 3. The needle protection device of FIGS. 3 and 4 is attached to vial 46 as follows. First, base 34 is slipped over vial 46. Once the desired placement of base 34 with respect to somewhere along the length of vial 46 is reached, arms 36 and 38 are squeezed together until the coacting hooked and blunt ends snap together to thereby secure base 42 to vial 46. Thus secured, the sheath (not shown) that covers needle 50 could then be removed. The securing of base 34 to vial 46 of course is done before vial 46 is fitted within housing 54 of injection applicator 52.

To assemble vial 46 to applicator 52, base 60 is turned counterclockwise so as to lower cylinder 58 to its lowermost position within body 54. Vial 46, with neck 44 of the protection device facing the reader, is inserted into body 54 of applicator 52 so that interlocked arms 36 and 38 extend through aperture 53. Thereafter, rod 64 is turned so that screw 24 is threadingly fitted to head 66 of push rod 64. Base 60 is then rotated clockwise so as to raise cylinder 58 to thereby force hub 48 of vial 46 against the top inner surface of body 54. Once base 60 is turned fully clockwise, due to the interaction between groove 62 and the not shown protrusion of base 56, vial 46 is tightly fitted within body 54. Thereafter, the vial device shown in FIG. 5 is usable. To discard vial 46, the reverse process is performed.

In operation, the clinician pricks the patient with needle 50, pushes the applicator rod 64 of injection applicator 52 forwards so as to cause rubber gasket 22 to push, and therefore inject, the medicament stored in vial 46 to the patient. After needle 50 is withdrawn from the patient, as was done in the device embodiment of FIGS. 1 and 2, housing 6 is pivoted to envelop needle 50; and hook 18 within housing 6, once snapped over needle 50, will fixedly retain needle 50 within housing 6, thereby preventing needle 50 from further being exposed to the environment. Thereafter, vial 46 is unthreaded from head 66 by turning push rod 64 in a counterclockwise direction. Cylinder 58 is then lowered by turning base 60 counterclockwise. Once cylinder 58 is moved to its lowermost position, vial 46, with its contaminated needle 50 being maintained and insulated within housing 6, is removed from body 54 and discarded in the appropriate manner.

It should be appreciated that the present invention is subject to many variations, modifications and changes in detail. Thus, it is the intention of the inventor that all matter described throughout this specification and shown in the accompanying drawings be interpreted as illustrative only and not in a limiting sense. Accordingly, it is intended that this invention be limited only by the spirit and scope of the hereto appended claims.

What is claimed is:

1. Needle protection apparatus, comprising:
   a vial;
   a needle mated to said vial;
   a substantially circular base positioned about said vial, said base including two coacting arms, said base to be placed around said vial when said two arms are not in coacting relationship with each other, said arms being pressed into a locking relationship to thereby fixedly attach said base to said vial once said base is appropriately placed around said vial;
   a housing flexibly connected to said base, said housing pivotable towards said needle;
   wherein once said base is fixedly attached to said vial, said housing is pivoted to be in alignment with said needle to cover said needle.

2. Needle protection apparatus of claim 1, wherein one of said arms has at its end thereof a hook extension that snaps onto the end of the other of said arms when said arms are pushed towards each other to thereby lock said base into position around said vial.

3. Needle protection apparatus of claim 2, wherein said arms each have a shoulder extending towards the other arm so that when said arms are pushed towards each other, the shoulders of said arms prevent said arms from being compressed beyond a given point to thereby ensure that further compressing of said arms will not free the end of said other arm from said hook extension of said one arm.

4. A needle protection device, comprising:
   a clamp-like base having two integral arms extending away from said base, one of said arms having a first end that coacts with a second end of the other of said arms when said arms are moved towards each other, said arms being locked with each other when said first end mates with said second end as said arms are pressed together to surround a vial wherefrom a needle extends, said base being fixedly coupled to said vial when said arms are locked with each other; and
   a housing flexibly extending from said base and pivotable to a position along the longitudinal axis of said vial, said housing being configured to prevent said needle from being exposed to the environment when it is pivoted to said position.

5. Needle protection device of claim 4, wherein said first end comprises a hooked extension and said second end comprises a blunt extension, said hooked and blunt extensions being locked when said hooked extension snaps over said blunt extension.

6. Needle protection device of claim 4, wherein said housing comprises a hook integral of said housing that locks onto said needle to thereby prevent further relative movement between said needle and said housing when said housing is pivoted to said position.

7. Apparatus for use with a vial to be mated with an applicator, comprising:
   a base having two arms extending away from said base, said arms lockable with each other about the body of said vial wherefrom a needle extends when said arms are moved towards each other, said base being fixedly coupled to the body of said vial when said arms are locked with each other; and
   a housing pivotally extending from said base and pivotable to a position along the longitudinal axis of said vial to envelop said needle extending from said vial.

8. Apparatus of claim 7, wherein said housing comprises a hook integral of said housing that locks onto said needle to thereby prevent further relative movement between said needle and said housing when said housing is pivoted to said position to envelop said needle.

9. Apparatus of claim 7, wherein one of said arms comprises a hooked extension and wherein other of said arms comprises a blunt extension, said hooked and blunt extensions being locked together when said hooked extension snaps over said blunt extension as said one and other arms are moved towards each other.

10. Apparatus of claim 7, wherein said arms each have a shoulder extending towards the other arm so that when said arms are pushed towards each other, the shoulders of said arms prevent said arms from being compressed beyond a given point to thereby ensure that further compressing of said arms will not free said arms from each other once said arms are locked together.

* * * * *